United States Patent
Fujimoto et al.

(10) Patent No.: US 11,976,394 B2
(45) Date of Patent: May 7, 2024

(54) NON-WOVEN FABRIC

(71) Applicant: Asahi Kasei Kabushiki Kaisha, Tokyo (JP)

(72) Inventors: Yuya Fujimoto, Tokyo (JP); Rumina Obi, Tokyo (JP); Takashi Komatsu, Tokyo (JP); Eiji Shiota, Tokyo (JP)

(73) Assignee: Mitsui Chemicals Asahi Life Materials Co., Ltd., Tokyo (JP)

( * ) Notice: Subject to any disclaimer, the term of this patent is extended or adjusted under 35 U.S.C. 154(b) by 0 days.

(21) Appl. No.: 17/638,312

(22) PCT Filed: Sep. 18, 2020

(86) PCT No.: PCT/JP2020/035586
§ 371 (c)(1),
(2) Date: Feb. 25, 2022

(87) PCT Pub. No.: WO2021/054465
PCT Pub. Date: Mar. 25, 2021

(65) Prior Publication Data
US 2022/0325453 A1 Oct. 13, 2022

(30) Foreign Application Priority Data
Sep. 20, 2019 (JP) .................. 2019-171821

(51) Int. Cl.
*D04H 1/4391* (2012.01)

(52) U.S. Cl.
CPC ..... *D04H 1/43918* (2020.05); *D10B 2401/12* (2013.01); *D10B 2509/00* (2013.01)

(58) Field of Classification Search
CPC .... D04H 1/43918; D04H 3/007; D04H 3/011; D10B 2401/12; D10B 2509/00
See application file for complete search history.

(56) References Cited

U.S. PATENT DOCUMENTS

| 4,783,231 A | 11/1988 | Raley |
| 5,997,980 A | 12/1999 | Matoba et al. |
(Continued)

FOREIGN PATENT DOCUMENTS

| CN | 1547631 A | 11/2004 |
| ID | 19916 A | 8/1998 |
(Continued)

OTHER PUBLICATIONS

English translation of WO-2016027493-A1 to Kasahara et al. obtained from PE2E database (Year: 2016).*

(Continued)

*Primary Examiner* — Jeremy R Pierce
(74) *Attorney, Agent, or Firm* — Morgan, Lewis & Bockius LLP (57) ABSTRACT

Provided is a non-woven fabric which is suitable for cleaning wipers, diapers, food packaging materials, etc., and has excellent water absorption and handling performance. The non-woven fabric according to the present invention contains a thermoplastic biodegradable resin, and is characterized in that fibers constituting the non-woven fabric have crimps, the flexural rigidity index in the mechanical direction (MD) of the non-woven fabric is 7.77-37.4 as defined by the following equation: flexural rigidity index in the mechanical direction (MD)=flexural rigidity (gf·cm) in the mechanical direction (MD)/{basis weight(g/m$^2$)}$^{2.5}$×10$^6$, and the bulk density of the non-woven fabric is 0.098 g/cm$^3$ to 0.251 g/cm$^3$.

9 Claims, 1 Drawing Sheet

(56) References Cited

U.S. PATENT DOCUMENTS

| | | |
|---|---|---|
| 2003/0021951 A1 | 1/2003 | Desai et al. |
| 2003/0148688 A1 | 8/2003 | Matsunaga |
| 2010/0304066 A1 | 12/2010 | Matsunaga |
| 2015/0183191 A1 * | 7/2015 | Nhan ...................... B32B 5/142 156/308.2 |

FOREIGN PATENT DOCUMENTS

| | | |
|---|---|---|
| JP | H07-34369 A | 2/1995 |
| JP | H07-034369 A | 2/1995 |
| JP | H07-279027 A | 10/1995 |
| JP | H08-260323 A | 10/1996 |
| JP | H09-013259 A | 1/1997 |
| JP | H09-095849 A | 4/1997 |
| JP | H11-021752 A | 1/1999 |
| JP | H11-050377 A | 2/1999 |
| JP | 2000-234254 A | 8/2000 |
| JP | 2001-355170 A | 12/2001 |
| JP | 2004-314460 A | 11/2004 |
| JP | 2007-516027 A | 6/2007 |
| JP | 2015-518091 A | 6/2015 |
| JP | 2016-41858 A | 3/2016 |
| WO | 2005/040328 A1 | 5/2005 |
| WO | 2005/055797 A1 | 6/2005 |
| WO | 2013/105587 A1 | 7/2013 |
| WO | 2014/023090 A1 | 2/2014 |
| WO | WO-2016027493 A1 * | 2/2016 ............ A61F 13/15 |
| WO | 2016/152670 A1 | 9/2016 |
| WO | 2019/167851 A1 | 9/2019 |

OTHER PUBLICATIONS

Supplementary European Search Report issued in corresponding European Patent Application No. 20865829.4 dated Aug. 1, 2022.
International Search Report issued in corresponding International Patent Application No. PCT/JP2020/035586 dated Dec. 1, 2020.
International Preliminary Report on Patentability and Written Opinion issued in corresponding International Patent Application No. PCT/JP2020/035586 dated Mar. 31, 2022.

* cited by examiner

NON-WOVEN FABRIC

FIELD

The present invention relates to a non-woven fabric.

BACKGROUND

Traditionally, sheets having high water absorption performance have been used in applications such as cleaning wipes, diapers, and food packaging materials. In cleaning wipes, for home and business uses, cleaning cloths composed of a non-woven fabric used to collect and remove various dust and hair from floors, walls, ceilings, furniture, machinery, etc., are commonly used, particularly as a disposable cleaning sheet suitable for cleaning wooden floors (flooring), which have been increasing rapidly as floors in various residential rooms. In diapers, such sheets are mainly used for top sheets and back sheets. In food packaging materials, since there are increasing opportunities to use microwave ovens to cook and reheat foods in the food service industry, convenience stores, and homes in recent years, such sheets are used, for example, in food packaging bags for microwave ovens because they have an excellent ability to retain moisture due to steam generated by heating.

However, it is necessary that such sheets exhibit bulkiness in order to exhibit water absorption performance, and as a result, there is a drawback in that the sheet becomes excessively soft, whereby the handling performance in the processing processes of the sheet and at the time of actual use are inferior, and there is a problem that usability is deteriorated.

Patent Literature 1 below discloses a method for the production of a non-woven fabric, wherein by using polypropylene as a raw material and producing a sheet by the spunbond method using a spinneret having a V-shaped cross-section nozzle, the yarns are crimped, which brings about bulkiness. However, under the production conditions described in Patent Literature 1, the sheet becomes extremely soft and the handling performance is significantly deteriorated. Furthermore, since the sheet is composed of polypropylene, the water absorption thereof is insufficient.

Further, Patent Literature 2 below discloses a non-woven fabric which, by focusing on the parameters of flexural rigidity and thickness and providing sufficient strength, does not cause scratches on the surface of a thin metal plate when wound between layers of a thin metal plate which is wound at high speed into a coil. However, Patent Literature 2 does not disclose a technique for achieving both handleability and water absorption performance required for a sheet used for cleaning wipes, diapers, and food packaging materials.

CITATION LIST

Patent Literature

[PTL 1] Japanese Unexamined Patent Publication (Kokai) No. 11-50377
[PTL 2] Japanese Unexamined Patent Publication (Kokai) No. 7-279027

SUMMARY

Technical Problem

In light of the problems of the prior art described above, an object of the present invention is to provide a non-woven fabric which has excellent water absorption and handling performance and which is suitable for applications such as cleaning wipes, diapers, and food packaging materials.

Solution to Problem

As a result of rigorous investigation in order to achieve the object described above, the present inventors have discovered that by using a thermoplastic biodegradable resin, ensuring bulkiness due to yarn crimping, and adopting a flexural rigidity within a certain range, both water absorption performance and handling performance are compatible, and have completed the present invention.

Specifically, the present invention is as described below.
[1] A non-woven fabric comprising a thermoplastic biodegradable resin, wherein fibers constituting the non-woven fabric have crimps, a machine direction (MD) flexural rigidity index of the non-woven fabric as defined by the following formula is 7.77 to 37.4:

machine direction (MD) flexural rigidity index=machine direction (MD) flexural rigidity $(\text{gf·cm})/\{\text{basis weight }(g/m^2)\}^{2.5} \times 10^6$, and a bulk density of the non-woven fabric is 0.098 $g/cm^3$ to 0.251 $g/cm^3$.
[2] The non-woven fabric according to [1], wherein a degree of deformation of the fibers is 1.2 to 2.2.
[3] The non-woven fabric according to [1] or [2], wherein the non-woven fabric has partially-bonded embossed parts, an interval of the embossed parts is 2.0 mm or more, and a bonding area ratio is 3% to 40%.
[4] The non-woven fabric according to any one of [1] to [3], wherein a work of compression WC of the non-woven fabric is 0.1 $gf·cm/cm^2$ or more.
[5] The non-woven fabric according to any one of [1] to [4], wherein a recoverability of compression RC of the non-woven fabric is 48% or more.
[6] The non-woven fabric according to any one of [1] to [5], wherein a basis weight of the non-woven fabric is 10 $g/m^2$ to 100 $g/m^2$.
[7] The non-woven fabric according to any one of [1] to [6], wherein the thermoplastic biodegradable resin is one selected from the group consisting of polylactic acid, polyhydroxyalkanoic acid, polyhydroxybutyrate variate, polyhydroxybutyrate hexanoate, nylon 4, polycaprolactone, polybutylene succinate, polybutylene succinate adipate, polybutylene terephthalate succinate, polybutylene succinate carbonate, polybutylene adipate terephthalate, polyethylene succinate, polyethylene terephthalate succinate, polyglycolic acid, and polyvinyl alcohol.
[8] The non-woven fabric according to any one of [1] to [6], wherein the thermoplastic biodegradable resin is two or more selected from the group consisting of polylactic acid, polyhydroxyalkanoic acid, polyhydroxybutyrate variate, polyhydroxybutyrate hexanoate, nylon 4, polycaprolactone, polybutylene succinate, polybutylene succinate adipate, polybutylene terephthalate succinate, polybutylene succinate carbonate, polybutylene adipate terephthalate, polyethylene succinate, polyethylene terephthalate succinate, polyglycolic acid, and polyvinyl alcohol.
[9] The non-woven fabric according to any one of [1] to [8], wherein the fibers constituting the non-woven fabric each have at least one recessed part inside a crimp in a single-fiber cross section, and a water absorption parameter as defined by the following formula is 4.7 or more:

water absorption parameter=$W \times S/B$ where W (wt %) is a water absorption rate of the fibers, B (g/cm$^3$) is a bulk density of the non-woven fabric, and S ($10^{-4}$ mm$^2$) is a cross-sectional area of the recessed part.

[10] The non-woven fabric according to any one of [1] to [9], wherein the non-woven fabric is a filament non-woven fabric.

[11] A cleaning wipe comprising the non-woven fabric according to any one of [1] to [10].

Advantageous Effects of Invention

The non-woven fabric of the present invention has excellent water absorption and handling performance and is suitable for applications such as cleaning wipes, diapers, and food packaging materials.

DESCRIPTION OF EMBODIMENTS

The embodiments of the present invention will be described in detail below.

The non-woven fabric of the present embodiment is a non-woven fabric comprising a thermoplastic biodegradable resin, wherein fibers constituting the non-woven fabric have crimps, a machine direction (MD) flexural rigidity index of the non-woven fabric as defined by the following formula is 7.77 to 37.4:

machine direction (MD) flexural rigidity index=machine direction (MD) flexural rigidity (gf·cm)/{basis weight (g/m$^2$)}$^{2.5}$×10$^6$, and a bulk density of the non-woven fabric is 0.098 g/cm$^3$ to 0.251 g/cm$^3$.

The non-woven fabric of the present embodiment can be a filament non-woven fabric. "Filament non-woven fabric" is a fabric as defined in JIS-L-0222. The non-woven fabric of the present embodiment, in the case of a filament non-woven fabric, can be provided by a known production method. However, from the viewpoint of ease of crimp formation, a so-called "melt-spun spunbond non-woven fabric", in which a thermoplastic synthetic resin is spun, the obtained filaments are laminated on a collection surface of a web conveyor or the like to form a web, and then partially bonded and integrated, is preferable.

In the non-woven fabric of the present embodiment, the fibers constituting the non-woven fabric have crimps. The phrase "have crimps" indicates a state in which the fibers are individually shrunk and rolled. By including crimps, the bulkiness is enhanced and the water absorption performance is improved. Furthermore, high flexibility is imparted, the ability to collect and remove large dust such as hair and animal hair is high, the degree of freedom of the fibers is high, and the effective adsorption area for fine particulates such as dust and soot is high.

The crimp number of the fibers is not particularly limited as long as the functions described above can be obtained, but from the viewpoint of increasing the bulkiness of the non-woven fabric and further improving water absorption, 5 crimps/inch or more is preferable, 10 crimps/inch or more is more preferable, and 18 crimps/inch or more is further preferable. When the crimp number is 5 crimps/inch or more, the free elongation distance of each fiber between the partial bonds of the non-woven fabric becomes long, the bulkiness of the non-woven fabric increases, the specific surface area of effective fibers increases, and the water absorption capacity tends to increase. Furthermore, though the upper limit of the crimp number is not particularly limited, it is generally difficult to obtain 50 or more crimps/inch in manufacturing.

When the non-woven fabric of the present embodiment is a filament non-woven fabric, the crimps of the fibers constituting the non-woven fabric may be so-called "latent crimps" which are expressed by heating, stretching, or solvent treatment after spinning, or may be so-called "actual crimps" which are expressed by spinning and deposition on a collection surface such as a web conveyor. However, it is desirable that actual crimps be used because dimensional changes are unlikely to occur during processing, basis weight variations are less likely to occur, and a homogeneous fabric-like sheet can be easily obtained.

In the non-woven fabric of the present embodiment, the fibers constituting the non-woven fabric are composed of a thermoplastic biodegradable resin. Since thermoplastic biodegradable resins have a certain level of hydrophilicity and moderate hardness, by constructing the non-woven fabric from fibers comprising a thermoplastic biodegradable resin, a non-woven fabric having excellent water absorption and handleability can be produced. Examples of the thermoplastic biodegradable resin include polylactic acid, polyhydroxyalkanoic acid, polyhydroxybutyrate variate, polyhydroxybutyrate hexanoate, nylon 4, polycaprolactone, polybutylene succinate, polybutylene succinate adipate, polybutylene terephthalate succinate, polybutylene succinate carbonate, polybutylene adipate terephthalate, polyethylene succinate, polyethylene terephthalate succinate, polyglycolic acid, and polyvinyl alcohol. Note that depending on the resin selected, household composting and marine composting are also possible.

Furthermore, the resin contained in the fibers constituting the non-woven fabric of the present embodiment may be a single component or a mixed component. Specifically, two or more types of the thermoplastic biodegradable resins described above can be combined.

In the case of a single component, micro and macro performance variations inside the yarn are reduced, uniformity is increased, and local deterioration of physical properties can be suppressed. Furthermore, in the case of a single component, stable spinning is more easily realized.

In the case of a mixed component, the content ratio of the sub-component to the main component is generally 2 wt % to 50 wt %, and preferably 5 wt % to 30 wt %. The form as a mixed component may be a simple polymer blend, a sheath-core composite composed of different resins, or a side-by-side composite. At this time, by using a low melting point component as the resin exposed on the surface, the compression bonding force in heat embossing is improved, and it is possible to bond at low temperatures or in high-speed transfer. Further, it is also possible to partially express the resin-derived characteristics by including a plurality of types of resins in the fibers with a sea-island structure.

Regarding two-component systems which include a low melting point component as a sub-component, by setting the temperature difference between the melting points or softening points between the two components to 20° C. or more, only sub-components having a low melting point are melted by heat-processing and the constituent fibers are bound to each other, whereby the main component can maintain fiber morphology and the mechanical strength of the non-woven fabric can be improved without being influenced by heat. Furthermore, the thermal processing conditions for melting only the sheath portion and maintaining the fiber morphology only for the main component can easily be controlled.

As the resin used in the two-component system, polylactic acid having a controlled melting point can be used. Since the lactic acid monomer has optically active carbon and optical isomers of D-lactic acid and L-lactic acid are present, the melting point of the polymer can be controlled by adjusting the copolymerization ratio of D-lactic acid and L-lactic acid. For example, the melting point of the polylactic acid can be controlled, such as when 1 mol % of D-lactic acid is copolymerized with L-lactic acid, the melting point becomes 170° C., when 3 mol % of D-lactic acid is copolymerized, the melting point becomes 150° C., when 6 mol % of D-lactic acid is copolymerized, the melting point becomes 140° C., and when 12 mol % of D-lactic acid is copolymerized, the melting point becomes 110° C.

The transverse-sectional shape (cross-sectional shape orthogonal to the longitudinal direction of the fibers) of the fibers constituting the non-woven fabric of the present embodiment is not limited to round and irregular cross-sections (flat, elliptical, polygonal, 3 to 14 leaves, T-shaped, V-shaped, Y-shaped), which are common solid cross-sections, but may be a hollow cross-sectional shape. From the viewpoint of crimp expression, it is preferable that there be a difference in the cooling rate in the yarn cross section immediately after spinning, and in general, the cooling difference in the yarn cross section is more likely to occur in deformed cross-sections.

If the fibers constituting the non-woven fabric of the present embodiment have a non-circular irregular cross-section, the specific surface area of the fibers in the non-woven fabric will be high, the area for adsorbing water and oil will also be large, whereby the water absorption capacity will be increased, which is preferable. The preferable degree of deformation of the deformed cross-section fibers is 1.2 to 2.2 from the viewpoints of absorption performance for liquids such as moisture, ease of fiber production, and stable productivity. When the degree of deformation is 1.2 or more, the above-mentioned adsorption area becomes large, and crimps are likely to be formed, which brings about bulkiness, whereby the water absorption capacity is excellent. Conversely, when the degree of deformation is 2.2 or less, the production stability of the non-woven fabric such as spinnability is excellent.

Figure 1:
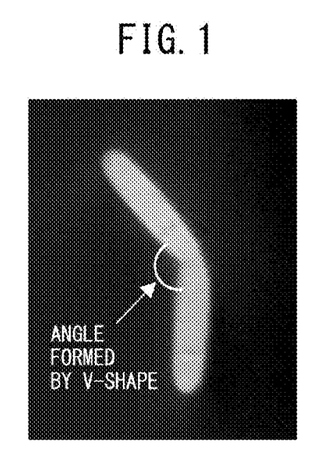
FIG. 1 shows the angle formed by a V-shaped cross-section in a single-fiber cross-section of a fiber constituting a non-woven fabric.
Figure 2:
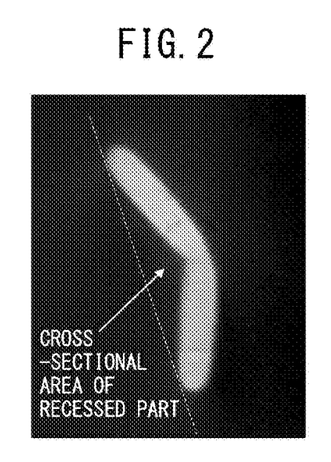
FIG. 2 shows a cross-sectional area of a recessed part inside a crimp in a single-fiber cross-section of a fiber constituting a non-woven fabric.

As shown in FIGS. 1 and 2, from the viewpoint of water absorption, it is preferable that the fibers constituting the non-woven fabric of the present embodiment each have at least one recessed part inside a crimp in a cross-section. When the single-fiber cross-section is V-shaped, the angle formed by the V-shape is preferably 30° or more, and more preferably 45° or more. When the angle is 30° or more, the cross-sectional area of the recessed part becomes large, and sufficient water absorption for wipes and diapers can be easily obtained. The angle is preferably 150° or less, and more preferably 120° or less. When the angle is 150° or less, crimps are sufficiently expressed and the cross-sectional area of the recessed part is also large, whereby sufficient liquid absorbency for wipes and diapers can be easily obtained.

When the bulk density of the non-woven fabric is defined as B (g/cm$^3$), the water absorption rate is defined as W (wt %), and the cross-sectional area of the recessed parts is S (10$^{-4}$ mm$^2$), the water absorption parameter as defined by the following formula is preferably 4.7 or more:

$$\text{water absorption parameter} = WS/B$$

When the water absorption parameter is 4.7 or more, since the water absorption ratio is stable and exceeds 1.3-times, the influence of variations in product performance are reduced, and the liquid absorption property is suitable in applications such as cleaning wipes and diapers. The water absorption parameter is more preferably 7.6 or more, and further preferably 9.9 or more.

In the non-woven fabric of the present embodiment, it is preferable that a part of the intersection of the fibers constituting the non-woven fabric be partially joined. Though adhesive bonding, ultrasonic bonding, partial hot air bonding, air-through bonding, or needle-punch bonding can be used as the bonding method, from the viewpoint of controlling the bulk density and flexural rigidity, partial thermocompression bonding by embossing is preferable. As the embossing process, a method of partial thermocompression bonding between an embossing roller and a flat roller is preferable.

In the embossing with an embossing roller and a flat roller, the temperature (surface temperature) of the partial thermocompression bonding can be selected in accordance with the melting point or softening point of the fibers, and for example, a temperature which is 10° C. to 80° C. lower than the melting point is preferable, and a temperature which is 30° C. to 60° C. lower is more preferable. When the partial thermocompression bonding temperature is in the temperature range of 10° C. to 80° C. lower than the melting point of fibers, the fibers do not excessively adhere to each other, whereby the bulkiness tends to increase, the fibers are sufficiently softened, and the fibers can easily be bonded to each other. As used herein, the temperature of the partial thermocompression bonding means not the set condition temperature but rather the actual temperature on the surface to be partially thermocompression bonded. Thus, when the atmospheric temperature around the machine is low, such as in the winter, it is necessary to raise the actual temperature around the machine by raising the set temperature condition or raising the atmospheric temperature. The thermocompression bonding pressure (linear pressure) is preferably 10 N/mm to 100 N/mm, and more preferably 10 N/mm to 40 N/mm.

In the non-woven fabric of the present embodiment, from the viewpoint of improving water absorption while increasing the handleability as a fabric, it is preferable that the interval of the embossed part be 2.0 mm or more and the bonding area ratio be 3% to 40%. "Bonding area ratio" refers to the ratio of the area of the adhered portions to the area of the non-woven fabric. In order to control the interval and bonding area ratio of the embossed part, the pattern, pitch, repeat, depth, etc., of the embossing roller may be adjusted.

Furthermore, though the larger the angle between the pins of the embossing roller and the roller surface, the more points the threads adhere to each other, which increases the flexural rigidity, since there is a limit to durability depending on the distance from the adjacent embossing, the optimum angle may be selected in accordance with the pitch, repeat, and bonding area ratio.

The embossing roller pattern may be a textured pattern, a silk pattern, a hexagonal pattern, or a point pattern, and is not particularly limited. At the time of thermocompression bonding, a clearance roller which can maintain thickness by providing a gap between the rollers may be used.

The fineness of the fibers constituting the non-woven fabric of the present embodiment is preferably 0.1 dtex to 5.0 dtex, and more preferably 0.1 dtex to 4.0 dtex. When the fineness is 5.0 dtex or less, crimps are more easily expressed and become bulky, and water absorption is likely to be high due to capillary action. Furthermore, for example, in a wipe application, a sufficient effective specific surface area of fibers can be obtained, which satisfies the collection performance for fine dust. Conversely, when the fineness is 0.1 dtex or more, the strength of the fibers is improved, the sheet is less likely to tear during processing processes or actual use, and the fibers are less likely to break and fall off.

The machine direction (MD) flexural rigidity index of the non-woven fabric of the present embodiment, as defined by the following formula, is 7.77 to 37.4, preferably 7.77 to 30.8, and more preferably 7.77 to 25.6:

machine direction (MD) flexural rigidity index=machine direction (MD) flexural rigidity (gf·cm)/{basis weight (g/m$^2$)}$^{2.5}$×10$^6$ When the flexural rigidity index is 7.77 to 37.4, the non-woven fabric has a suitable hardness and has good handleability in applications such as cleaning wipes, diapers, and food packaging materials.

The bulk density of the non-woven fabric of the present embodiment is preferably 0.098 g/cm$^3$ to 0.251 g/cm$^3$, preferably 0.098 g/cm$^3$ to 0.236 g/cm$^3$, and more preferably 0.098 g/cm$^3$ to 0.193 g/cm$^3$. When the bulk density is 0.098 g/cm$^3$ or more, the bulkiness is sufficient and excellent water absorption ability is likely to be developed. Furthermore, the fiber gap is not excessively large, whereby the wiping surface is less likely leave contaminants behind, for example, in wipe applications. Conversely, when the bulk density is 0.290 g/cm$^3$ or less, the fibers gap is not excessively small, and for example, in wipe applications, solids can easily be collected. The bulk density is a value obtained by dividing the basis weight of the non-woven fabric by thickness and converting the unit to g/cm$^3$.

The basis weight of the non-woven fabric of the present embodiment is not particularly limited and is preferably 10 g/m$^2$ to 100 g/m$^2$, and further preferably 10 g/m$^2$ to 80 g/m$^2$. When the basis weight is 10 g/m$^2$ or more, it is easy to obtain the strength of the sheet practically sufficient for applications such as cleaning wipes, diapers, and food packaging materials. Conversely, if it is 100 g/m$^2$ or less, it is sufficiently thin and the handleability in actual use is suitable.

The work of compression (WC) of the non-woven fabric of the present embodiment is preferably 0.1 gf·cm/cm$^2$ or more, and preferably 1.0 gf·cm/cm$^2$ or less. When the work of compression (WC) is 0.1 gf·cm/cm$^2$ or more, the non-woven fabric is soft and easily compressed, and the bulkiness is easily developed.

The recoverability of compression (RC) of the non-woven fabric of the present embodiment is preferably 48% or more, and preferably 75% or less. When it is 48% or more, for example, when used as a cleaning wipe, it is excellent in water absorption because it can utilize the potential voids (bulky), and the cleaning ability can easily be maintained. Furthermore, in diaper applications, there is an advantage that bulkiness (volume) during wearing can be maintained for a long time.

The non-woven fabric of the present embodiment is also excellent in liquid absorption performance for liquids other than water, for example, liquids such as oil and alcohols. Specifically, since it has excellent liquid absorption performance for liquids such as urine, soaps, detergents, cleaning agents, window cleaning agents, bactericides, biocides, abrasives, friction materials, neutralizers, insect repellents, paint solvent, paint removers, finish removers, oil solvents, grease solvents, makeup removers, stain removers, dyes, paints, varnishes, waxes, and polishes, it can suitably be used for various cleaning wipes, diapers, and food packaging materials.

The non-woven fabric of the present embodiment may contain a surfactant from the viewpoint of antistatic property and expression of water absorption. Any nonionic, anionic, or cationic system may be used as the surfactant, and carboxylic acid type, sulfonic acid type, sulfate ester type, phosphoric acid ester type, ester type, ether type, ester ether type, alkanolamide type, alkylamine type, or quaternary ammonium type surfactants can be used. Ester types are preferable, and among ester types, sorbitan fatty acid esters, polyglycerin fatty acid esters, and polyoxyalkylene alkyl esters are particularly preferable. Furthermore, these surfactants may be used alone or in combination.

The adhesion rate of the surfactant is preferably 0.1 wt % or more, and more preferably 2.0 wt % or less with respect to the weight of the non-woven fabric from the viewpoint of sufficient antistatic and water absorption properties. When the adhesion rate of the surfactant is 0.1 wt % or more and 2.0 wt % or less, sufficient performance can be obtained.

As the surfactant application method, any method such as the Kiss method, gravure method, spray method, etc., can be adopted, and the method can be appropriately selected in accordance with purpose. Specifically, when it is desired to develop the performance on only one side, a transfer method such as the Kiss method or gravure method is preferable, and when it is desired to obtain the same performance on both sides, a coating method by a spray method is preferable.

EXAMPLES

The present invention will be specifically described below by way of the following Examples and Comparative Examples. The present invention is not limited in any manner by these examples. Note that the measurement methods and evaluation methods used are as described below.

(1) Fineness (dtex)

30 or more 1 m fibers collected by spinning are prepared and the weights thereof are measured. This is converted to a weight of 10000 m. When determining fineness from a cloth-like sample, the cross section of the sample is observed using an electron microscope, and the cross-sectional area of the threads is converted into a weight of 10000 m by multiplying the average value measured at N=10 by the specific weight. In the case of staples, fineness can be measured by a known method.

(2) Degree of Deformation

The cross section of the sample (fibers collected from a non-woven fabric) is observed using an electron microscope, the cross section and circumference of the deformed fibers at N=10 are measured, and the cross-sectional area and perimeter of deformed fibers are obtained from the average values thereof. Next, the radius of a perfect circle having the same cross-sectional area as the cross-sectional area of the deformed fibers is calculated, the circumference of the perfect circle having the same cross-sectional area as the deformed fibers is calculated from the radius, and the degree of deformation is determined from the following formula:

Degree of deformation=perimeter of deformed fibers/perimeter of perfect circle having same cross-sectional area as deformed fibers.

(3) Crimp Number (Crimps/Inch (2.54 cm))

The crimp number is measured according to JIS L 1015: 2010 "Chemical fibers staple test method." When the crimp number is determined from a cloth-like sample, the longest possible thread is sampled, the crimp number is measured at N=10, and the crimp number is converted into a crimp number per inch.

(4) Fiber Water Absorption Rate (wt %)

The official moisture content of each resin constituting the fibers constituting the non-woven fabric is defined as the water absorption rate. In particular, the water absorption rate of polylactic acid is 0.5 wt %, polyhydroxyalkanoic acid (including polyhydroxybutyrate variate and polyhydroxybutyrate hexanoate) is 0.4 wt %, nylon 4 is 1.7 wt %, polycaprolactone is 0.5 wt %, polybutylene succinate (including polybutylene succinate adipate, polybutylene terephthalate succinate, polybutylene succinate carbonate, polybutylene adipate terephthalate, polyethylene succinate, and polyethylene terephthalate succinate) is 0.33 wt %, and polyglycolic acid is 0.4 wt %. Furthermore, the water absorption rate of polypropylene is 0.02 wt %. In the case of a two-component blend, the surface exposure rate of the sub-component is set to 20% of the addition rate, and the total exposure rate of each resin is used. For example, in the case of a blend of 90% polylactic acid and 10% polybutylene succinate, the water absorption rate is calculated as 0.33×(0.1×0.2)+0.5×(1−0.1×0.2).

(5) Angle Formed by V-Shaped Cross-Section (°)

The single-fiber cross-section of the fibers constituting the non-woven fabric is photographed with an electron microscope, the angle (°) formed by the V-shape shown in FIG. 1 is measured at N=10, and the average value is calculated.

(6) Cross-Sectional Area of Recessed Part of Single-Fiber Cross-Section ($\times 10^{-4}$ mm$^2$)

A single-fiber cross-section is photographed with an electron microscope, the cross-sectional area of the recessed part shown in FIG. 2 is measured at N=10, and the average value is obtained. The cross-sectional area of the single-fiber cross-section recessed part is the area in the electron microscope photograph of the single-fiber cross-section when a single straight line is drawn so that the area surrounding the single yarn and a single straight line in contact with the single yarn is the greatest.

(7) Basis Weight (g/m$^2$)

20 cm length×25 cm width samples are cut from three locations, the weights thereof are measured, and the average value is converted into a mass per unit (JIS-L-1906).

(8) Thickness (mm)

The thickness at 100 g load is measured using a thickness meter manufactured by Mitsutoyo Corporation.

(9) Bulk Density of Non-Woven Fabric (g/cm$^3$)

The bulk density of the non-woven fabric is a value obtained by dividing the basis weight of the non-woven fabric by the thickness and converting the unit into g/cm$^3$.

(10) Water Absorption Parameter of Non-Woven Fabric

When the fibers constituting the non-woven fabric each have at least one recessed part inside a crimp in a single-fiber cross section, the water absorption parameter is determined from the following formula:

$$\text{water absorption parameter} = W \times S/B$$

where W (wt %) is a water absorption rate of the fibers, B (g/cm$^3$) is a bulk density of the non-woven fabric, and S ($10^{-4}$ mm$^2$) is a cross-sectional area of the recessed part.

(11) KES Flexural Rigidity (gf·cm), Machine Direction (MD) Flexural Rigidity Index, CD Direction Flexural Rigidity Index A KES/FB2-AUTO-A manufactured by Kato Tech Co., Ltd., is used as the measurement device. The sample is 20 cm×20 cm and the KES flexible rigidity is measured. The machine direction (MD) flexural rigidity index is calculated from the following formula:

$$\text{machine direction (MD) flexural rigidity index} = \text{machine direction (MD) flexural rigidity (gf·cm)} / \{\text{basis weight (g/m}^2)\}^{2.5} \times 10^6.$$

The CD direction flexural rigidity index is calculated in the same manner.

(12) KES Work of Compression (WC) [gf·cm/cm$^2$]

A KES (KES-G5) manufactured by Kato Tech Co., Ltd., is used as the measurement device. The KES work of compression is measured. Note that work of compression is a value obtained by reading INT and B of the integrated voltage and multiplying them by 1/10. It is deemed that the greater the value, the greater the work of compression (bulk).

(13) KES Compression Recovery Amount (WC'), Recoverability of Compression (RC)

A KES (KES-G5) manufactured by Kato Tech Co., Ltd., is used as the measurement device. The KES recoverability of compression is measurement. The recoverability of compression (RC) is a value obtained by dividing the compression recovery amount WC' by the work of compression WC, and is represented by a percentage. The greater the value, the better the recoverability of compression.

(14) Water Absorption (Magnification)

The non-woven fabric is cut into a 10 cm square, which is stored at 20° C. and 65% RH for 12 hours, and then weighed with an electronic balance. The sample is placed on a mesh net, immersed in pure water for 30 seconds, and after 30 seconds, the mesh net and the sample are removed and allowed to stand horizontally for 10 minutes. Thereafter, the sample weight is measured and the water absorption ratio is calculated from the weights before and after immersion.

(15) Oil Absorption (Magnification)

The sample is cut into a 10 cm square, which is stored at 20° C. and 65% RH for 12 hours, and then weighed with an electronic balance. The sample is immersed in oil (Shell Terrace S2M32) for 30 seconds, removed, and allowed to stand until the liquid dropping interval is 15 seconds or longer. Thereafter, the sample weight is measured and the oil absorption ratio is calculated from the weights before and after immersion.

(16) Ethanol Liquid Absorption (Magnification)

The sample is cut into a 10 cm square, which is stored at 20° C. and 65% RH for 12 hours, and then weighed with an electronic balance. The sample is immersed in ethanol for 30 seconds, removed, and allowed to stand until the liquid no longer drops. Thereafter, the sample weight is measured, and the ethanol absorption ratio is calculated from the weights before and after immersion.

(17) Handleability

A clear file folder (composed of polyethylene) with four 10 mm thick×100 mm long lines drawn with a black magic marker is prepared. 500 μL of methyl ethyl ketone (MEK) is added dropwise to a sample cut into 10×3 cm pieces, and a portion thereof is used to wipe off the black magic marker lines. The handleability at that time is judged according to the following five evaluation criteria. The higher the number, the higher the handleability.

[Evaluation Criteria]
- 5: Rigidity is moderate, and gripping during wiping is suitable.
- 4: Rigidity is slightly low, and gripping during wiping is slightly suitable.
- 3: Rigidity is slightly high, and gripping during wiping is normal.
- 2: Rigidity is low or high, and gripping during wiping is slightly poor.
- 1: Rigidity is extremely low or extremely high, and gripping during wiping is poor.

(18) Cleaning Ability Sustainability

Cleaning ability sustainability when the handleability test is repeated five times is judged according to following evaluation criteria.

[Evaluation Criteria]
- Good: Sufficient liquid absorption of methyl ethyl ketone and the same load for cleaning as the first time.
- OK: Insufficient liquid absorption of methyl ethyl ketone and greater load for cleaning than the first time due to excessive liquid adhesion to the file folder.

(19) Industrial Compostability

Compostability measurement for up to 12 weeks is performed in accordance with the ISO 16929 (JIS K 6952) pilot scale aerobic disintegration degree measurement, the composted material is passed through a 2 mm opening mesh, and the following evaluation criteria are used to evaluate the ratio of the remaining weight after passing through the mesh to the weight before passing through the mesh.

[Evaluation Criteria]
- Excellent: 5% or less remained on mesh.
- Good: 5% or more and 10% or less remained on mesh.
- Poor: More than 10% remained on mesh.

Examples 1 to 14

Polylactic acid was discharged from a spunbonding spinneret at a spinning temperature of 220° C., the yarn was symmetrically cooled from both sides by a cooling device directly under the spinneret (each wind speed 0.5 m/s), and drawn by a draw jet to obtain crimped continuous filaments having a degree of deformation of 1.6 and a fineness of 2.3 dtex. These fibers were spread and dispersed on web conveyor to produce a web, and the web was thermocompression bonded between an embossing roller having an embossing interval of 4.43 mm and a flat roller at a bonding area ratio of 8% to obtain a non-woven fabric. In order to confirm the influence of the embossing temperature on a total basis weight of 10 to 100 g/m², the transport speed was arbitrarily adjusted to prepare unembossed raw fabrics which were then wound, and thereafter, thermocompression bonding was performed while changing the temperature of the embossing roller/flat roller from 90° C./90° C. to 120° C./120° C. under a constant embossing speed of 5 m/min and a linear pressure of 20 N/mm on a separate line, whereby the filament non-woven fabrics of Examples 1 to 14 were obtained.

Example 15

The filament non-woven fabric of Example 15 was obtained using crimped fibers having an average fineness of 1.7 dtex using the production method of Example 6, except that the drawing force by the draw jet was increased.

Example 16

The filament non-woven fabric of Example 16 was obtained using crimped fibers having an average fineness of 1.7 dtex using the production method of Example 6, except that in the cooling by the cooling device, the yarn was asymmetrically cooled from both sides (0.9 m/s and 0 m/s).

Example 17

The filament non-woven fabric of Example 17 was obtained using crimped fibers having an average fineness of 4.0 dtex using the production method of Example 6, except that the drawing force by the draw jet was decreased.

Examples 18 to 21

The filament non-woven fabrics of Examples 18 to 21 were obtained by changing the transfer speed in the fiber structure of Example 6 so that the basis weight was 52 g/m² while increasing the number of spinneret holes (discharge amount), performed embossing continuously, and changing the temperature of the embossing roller under each condition.

Examples 22 to 31

The filament non-woven fabrics of Examples 22 to 31 were obtained by changing the embossing pattern, bonding area ratio, pitch, repeat, and depth of the fiber structure of Example 6, and changing the transport speed so that the basis weight was 52 g/m².

Examples 32 to 39

The filament non-woven fabrics of Examples 32 to 39 were obtained under the same production conditions as Example 7, except that the single-fiber cross-sectional shape (angle formed by the V-shape) was changed.

Example 40

The filament non-woven fabric of Example 40 was obtained under the same production conditions as Example 6, except that the raw material was changed to polyhydroxyalkanoic acid (PHA), the spinning temperature was changed to 150° C., and the temperature of upper and lower embossing rollers was changed to 90° C.

Example 41

The filament non-woven fabric of Example 41 was obtained under the same production conditions as Example 6, except that the raw material was changed to polybutylene succinate (PBS), the spinning temperature was changed to 150° C., and the temperature of upper and lower embossing rollers was changed to 80° C.

Example 42

The filament non-woven fabric of Example 42 was obtained under the same production conditions as Example 6, except that the raw material was changed to polyglycolic acid (PGA), the spinning temperature was changed to 240° C., and the temperature of upper and lower embossing rollers was changed to 180° C.

Example 43

The filament non-woven fabric of Example 43 was obtained under the same production conditions as Example 6, except that the raw material was changed to nylon 4 (PA4), the spinning temperature was changed to 280° C., and the temperature of upper and lower embossing rollers was changed to 220° C.

Example 44

The filament non-woven fabric of Example 44 was obtained under the same production conditions as Example 21, except that 10% polyhydroxyalkanoic acid (PHA) was added to the polylactic acid and the temperatures of upper and lower embossing rollers were each lowered by 15° C. (135/135° C.).

Example 45

The filament non-woven fabric of Example 45 was obtained under the same production conditions as Example 21, except that 10% polybutylene succinate (PBS) was added to the polylactic acid and the temperatures of upper and lower embossing rollers were each lowered by 15° C. (135/135° C.).

Example 46

The filament non-woven fabric of Example 46 was obtained under the same production conditions as Example 21, except that 10% of a low melting point polylactic acid (melting point: 115° C.) obtained by copolymerizing 12 mol % of D-lactic acid with L-lactic acid was added to the polylactic acid and the temperatures of upper and lower embossing rollers were each lowered by 15° C. (135/135° C.).

As described above, the characteristics, etc., of the filament non-woven fabrics obtained in Examples 1 to 46 are shown in Tables 1 to 4 below.

TABLE 1

| | Item | Unit | Example 1 | 2 | 3 | 4 | 5 | 6 | 7 | 8 | 9 | 10 | 11 | 12 |
|---|---|---|---|---|---|---|---|---|---|---|---|---|---|---|
| Structure/ Production Method | Single or two-component | — | Single component | Single component | Single component | Single component | Single component | Single component | Single component | Single component | Single component | Single component | Single component | Single component |
| | Fiber cross-section | — | V-shape | V-shape | V-shape | V-shape | V-shape | V-shape | V-shape | V-shape | V-shape | V-shape | V-shape | V-shape |
| | Resin | — | PLA | PLA | PLA | PLA | PLA | PLA | PLA | PLA | PLA | PLA | PLA | PLA |
| | Roller temperature | ° C. | 90 | 100 | 110 | 120 | 90 | 100 | 110 | 120 | 90 | 100 | 110 | 120 |
| | Embossing linear pressure | N/mm | 20 | 20 | 20 | 20 | 20 | 20 | 20 | 20 | 20 | 20 | 20 | 20 |
| | Embossing temperature | m/min | 5 | 5 | 5 | 5 | 5 | 5 | 5 | 5 | 5 | 5 | 5 | 5 |
| | Embossing pattern | — | Pins | Pins | Pins | Pins | Pins | Pins | Pins | Pins | Pins | Pins | Pins | Pins |
| | Bonding area ratio | % | 8 | 8 | 8 | 8 | 8 | 8 | 8 | 8 | 8 | 8 | 8 | 8 |
| | Emboss depth | mm | 1.5 | 1.5 | 1.5 | 1.5 | 1.5 | 1.5 | 1.5 | 1.5 | 1.5 | 1.5 | 1.5 | 1.5 |
| | Embossing interval | mm | 4.43 | 4.43 | 4.43 | 4.43 | 4.43 | 4.43 | 4.43 | 4.43 | 4.43 | 4.43 | 4.43 | 4.43 |
| Fibers | Fineness | dtex | 2.3 | 2.3 | 2.3 | 2.3 | 2.3 | 2.3 | 2.3 | 2.3 | 2.3 | 2.3 | 2.3 | 2.3 |
| | Degree of irregularity | — | 1.6 | 1.6 | 1.6 | 1.6 | 1.6 | 1.6 | 1.6 | 1.6 | 1.6 | 1.6 | 1.6 | 1.6 |
| | Crimp number | crimps/inch | 18 | 18 | 18 | 18 | 18 | 18 | 18 | 18 | 18 | 18 | 18 | 18 |
| | Water absorption rate | wt % | 0.50 | 0.50 | 0.50 | 0.50 | 0.50 | 0.50 | 0.50 | 0.50 | 0.50 | 0.50 | 0.50 | 0.50 |
| | Angle formed by V-shape | ° | 120 | 120 | 120 | 120 | 120 | 120 | 120 | 120 | 120 | 120 | 120 | 120 |
| | Surface area of recessed part | $10^{-4} mm^2$ | 4.1 | 4.1 | 4.1 | 4.1 | 4.1 | 4.1 | 4.1 | 4.1 | 4.1 | 4.1 | 4.1 | 4.1 |
| Fabric | Basis weight | g/m² | 38 | 41 | 40 | 40 | 52 | 52 | 52 | 54 | 79 | 73 | 73 | 76 |
| | Thickness | mm | 0.23 | 0.28 | 0.24 | 0.26 | 0.30 | 0.29 | 0.34 | 0.36 | 0.61 | 0.35 | 0.35 | 0.37 |
| | Bulk density | g/cm³ | 0.162 | 0.145 | 0.166 | 0.155 | 0.175 | 0.177 | 0.156 | 0.151 | 0.129 | 0.211 | 0.209 | 0.202 |
| | MD | (gf · cm²/ | 11.2 | 13.8 | 14.4 | 16.6 | 13.4 | 15.6 | 12.3 | 13.7 | 7.8 | 15.3 | 14.5 | 12.1 |

TABLE 1-continued

| Item | Unit | Example 1 | 2 | 3 | 4 | 5 | 6 | 7 | 8 | 9 | 10 | 11 | 12 |
|---|---|---|---|---|---|---|---|---|---|---|---|---|---|
| direction flexural rigidity index | (cm)/$(g/m^2)^{2.5}$ | | | | | | | | | | | | |
| CD direction flexural rigidity index | $(gf \cdot cm^2/cm)/(g/m^2)^{2.5}$ | 4.08 | 5.80 | 4.87 | 9.04 | 5.72 | 9.91 | 8.19 | 7.35 | 3.28 | 9.60 | 8.57 | 8.65 |
| Work of compression WC | $gf \cdot cm/cm^2$ | 0.384 | 0.289 | 0.295 | 0.278 | 0.352 | 0.195 | 0.253 | 0.167 | 0.601 | 0.330 | 0.356 | 0.318 |
| Recoverability of compression RC | % | 64 | 70 | 71 | 71 | 58 | 64 | 64 | 65 | 48 | 66 | 65 | 68 |
| Water absorption parameter | — | 12.8 | 14.3 | 12.5 | 13.3 | 11.8 | 11.7 | 13.2 | 13.7 | 11.3 | 9.8 | 9.9 | 10.2 |
| Handleability | — | 5 | 5 | 5 | 5 | 5 | 5 | 5 | 5 | 4 | 5 | 5 | 5 |
| Water absorption | times | 1.4 | 1.3 | 1.3 | 1.3 | 1.5 | 1.5 | 1.6 | 1.5 | 1.4 | 1.3 | 1.3 | 1.3 |
| Oil absorption | times | 10.0 | 8.1 | 6.3 | 6.9 | 7.4 | 5.8 | 5.5 | 4.8 | 8.2 | 5.8 | 5.6 | 4.9 |
| Ethanol liquid absorption | times | 6.9 | 5.5 | 5.2 | 4.9 | 5.6 | 4.8 | 4.5 | 4.3 | 5.4 | 4.5 | 4.1 | 4.0 |
| Cleaning ability sustainability | — | Good | Good | Good | Good | Good | Good | Good | Good | Good | Good | Good | Good |
| Industrial compostability | — | Good | Good | Good | Good | Good | Good | Good | Good | Good | Good | Good | Good |

TABLE 2

| | Item | Unit | Example 13 | 14 | 15 | 16 | 17 | 18 | 19 | 20 | 21 | 22 | 23 | 24 |
|---|---|---|---|---|---|---|---|---|---|---|---|---|---|---|
| Structure/ Production Method | Single or two-component | — | Single component | Single component | Single component | Single component | Single component | Single component | Single component | Single component | Single component | Single component | Single component | Single component |
| | Fiber cross-section | — | V-shape | V-shape | V-shape | V-shape | V-shape | V-shape | V-shape | V-shape | V-shape | V-shape | V-shape | V-shape |
| | Resin | — | PLA | PLA | PLA | PLA | PLA | PLA | PLA | PLA | PLA | PLA | PLA | PLA |
| | Roller temperature | °C. | 100 | 100 | 100 | 100 | 100 | 120 | 130 | 140 | 150 | 100 | 100 | 100 |
| | Embossing linear pressure | N/mm | 20 | 20 | 20 | 20 | 20 | 20 | 20 | 20 | 20 | 20 | 20 | 20 |
| | Embossing temperature | m/min | 5 | 5 | 5 | 5 | 5 | 25 | 50 | 75 | 100 | 5 | 5 | 5 |
| | Embossing pattern | — | Pins | Pins | Pins | Pins | Pins | Pins | Pins | Pins | Pins | Pins | Pins | Pins |
| | Bonding area ratio | % | 8 | 8 | 8 | 8 | 8 | 8 | 8 | 8 | 8 | 3 | 8 | 8 |

TABLE 2-continued

| | Item | Unit | Example 13 | 14 | 15 | 16 | 17 | 18 | 19 | 20 | 21 | 22 | 23 | 24 |
|---|---|---|---|---|---|---|---|---|---|---|---|---|---|---|
| | Emboss depth | mm | 1.5 | 1.5 | 1.5 | 1.5 | 1.5 | 1.5 | 1.5 | 1.5 | 1.5 | 1.5 | 5.1 | 1.5 |
| | Embossing interval | mm | 4.43 | 4.43 | 4.43 | 4.43 | 4.43 | 4.43 | 4.43 | 4.43 | 4.43 | 4.43 | 4.43 | 12 |
| Fibers | Fineness | dtex | 2.3 | 2.3 | 1.7 | 1.7 | 4.0 | 2.3 | 2.3 | 2.3 | 2.3 | 2.3 | 2.3 | 2.3 |
| | Degree of irregularity | — | 1.6 | 1.6 | 1.6 | 1.6 | 1.6 | 1.6 | 1.6 | 1.6 | 1.6 | 1.6 | 1.6 | 1.6 |
| | Crimp number | crimps/inch | 18 | 18 | 25 | 32 | 10 | 18 | 18 | 18 | 18 | 18 | 18 | 18 |
| | Water absorption rate | wt % | 0.50 | 0.50 | 0.50 | 0.50 | 0.50 | 0.50 | 0.50 | 0.50 | 0.50 | 0.50 | 0.50 | 0.50 |
| | Angle formed by V-shape | ° | 120 | 120 | 120 | 120 | 120 | 120 | 120 | 120 | 120 | 120 | 120 | 120 |
| | Surface area of recessed part | $10^{-4}mm^2$ | 4.1 | 4.1 | 4.1 | 4.1 | 4.1 | 4.1 | 4.1 | 4.1 | 4.1 | 4.1 | 4.1 | 4.1 |
| Fabric | Basis weight | g/m² | 10 | 100 | 52 | 52 | 52 | 52 | 52 | 52 | 52 | 52 | 52 | 52 |
| | Thickness | mm | 0.08 | 0.52 | 0.46 | 0.53 | 0.25 | 0.32 | 0.33 | 0.34 | 0.33 | 0.34 | 0.34 | 0.38 |
| | Bulk density | g/cm³ | 0.125 | 0.192 | 0.113 | 0.098 | 0.211 | 0.164 | 0.159 | 0.154 | 0.157 | 0.155 | 0.155 | 0.137 |
| | MD direction flexural rigidity index | (gf·cm²/cm)/(g/m²)^{2.5} | 7.9 | 16.1 | 10.8 | 9.2 | 22.1 | 14.0 | 13.5 | 14.0 | 14.5 | 12.5 | 12.5 | 15.8 |
| | CD direction flexural rigidity index | (gf·cm²/cm)/(g/m²)^{2.5} | 3.48 | 9.70 | 6.67 | 4.62 | 14.36 | 7.52 | 8.02 | 8.02 | 7.67 | — | — | — |
| | Work of compression WC | gf·cm/cm² | 0.245 | 0.432 | 0.945 | 0.998 | 0.234 | 0.247 | 0.263 | 0.264 | 0.256 | 0.264 | 0.276 | 0.325 |
| | Recoverability of compression RC | % | 73 | 45 | 45 | 43 | 63 | 62 | 67 | 64 | 63 | 62 | 64 | 59 |
| | Water absorption parameter | — | 16.5 | 10.7 | 18.3 | 21.1 | 9.8 | 12.6 | 13.0 | 13.4 | 13.2 | 13.3 | 13.3 | 15.1 |
| | Handleability | — | 4 | 5 | 5 | 5 | 5 | 5 | 5 | 5 | 5 | 5 | 5 | 5 |
| | Water absorption | times | 3.3 | 1.3 | 2.2 | 2.8 | 1.5 | 1.6 | 1.7 | 1.6 | 1.6 | 1.6 | 1.6 | 1.8 |
| | Oil absorption | times | 21.0 | 5.3 | 9.0 | 10.7 | 4.9 | 5.2 | 5.3 | 5.5 | 5.8 | 5.4 | 5.5 | 6.2 |
| | Ethanol liquid absorption | times | 15.2 | 3.4 | 7.5 | 9.0 | 3.9 | 4.6 | 4.8 | 4.5 | 4.4 | 4.4 | 4.5 | 5.1 |
| | Cleaning ability sustainability | — | Good | OK | OK | OK | Good | Good | Good | Good | Good | Good | Good | Good |
| | Industrial compostability | — | Good | Good | Good | Good | Good | Good | Good | Good | Good | Good | Good | Good |

TABLE 3

| | | | Example | | | | | | | | | | | |
|---|---|---|---|---|---|---|---|---|---|---|---|---|---|---|
| | Item | Unit | 25 | 26 | 27 | 28 | 29 | 30 | 31 | 32 | 33 | 34 | 35 | 36 |
| Structure/ Production Method | Single or two-component | — | Single component | Single component | Single component | Single component | Single component | Single component | Single component | Single component | Single component | Single component | Single component | Single component |
| | Fiber cross-section | — | V-shape | V-shape | V-shape | V-shape | V-shape | V-shape | V-shape | V-shape | V-shape | V-shape | V-shape | V-shape |
| | Resin | — | PLA | PLA | PLA | PLA | PLA | PLA | PLA | PLA | PLA | PLA | PLA | PLA |
| | Roller temperature | °C. | 100 | 100 | 100 | 100 | 100 | 100 | 100 | 100 | 100 | 100 | 100 | 100 |
| | Embossing linear pressure | N/mm | 20 | 20 | 20 | 20 | 20 | 20 | 20 | 20 | 20 | 20 | 20 | 20 |
| | Embossing temperature | m/min | 5 | 5 | 5 | 5 | 5 | 5 | 5 | 5 | 5 | 5 | 5 | 5 |
| | Embossing pattern | — | Pins | Pins | Pins | Pins | Pins | Hexagonal | Oblique grid | Pins | Pins | Pins | Pins | Pins |
| | Bonding area ratio | % | 8 | 8 | 8 | 8 | 8 | 24.5 | 29 | 8 | 8 | 8 | 8 | 8 |
| | Emboss depth | mm | 1.5 | 1.5 | 1.5 | 0.64 | 0.42 | 1.1 | 1.2 | 1.5 | 1.5 | 1.5 | 1.5 | 1.5 |
| | Embossing interval | mm | 9 | 2 | 1.3 | 2 | 2 | 9 | 9 | 4.43 | 4.43 | 4.43 | 4.43 | 4.43 |
| Fibers | Fineness | dtex | 2.3 | 2.3 | 2.3 | 2.3 | 2.3 | 2.3 | 2.3 | 2.3 | 2.3 | 2.3 | 2.3 | 2.3 |
| | Degree of irregularity | — | 1.6 | 1.6 | 1.6 | 1.6 | 1.6 | 1.6 | 1.6 | 1.6 | 1.6 | 1.6 | 1.6 | 1.6 |
| | Crimp number | crimps/inch | 18 | 18 | 18 | 18 | 18 | 18 | 18 | 20 | 21 | 22 | 16 | 19 |
| | Water absorption rate | wt % | 0.50 | 0.50 | 0.50 | 0.50 | 0.50 | 0.50 | 0.50 | 0.50 | 0.50 | 0.50 | 0.50 | 0.50 |
| | Angle formed by V-shape | ° | 120 | 120 | 120 | 120 | 120 | 120 | 120 | 90 | 60 | 45 | 150 | 90 |
| | Surface area of recessed part | $10^{-4}$mm$^2$ | 4.1 | 4.1 | 4.1 | 4.1 | 4.1 | 4.1 | 4.1 | 4.8 | 4.1 | 3.4 | 2.4 | 5.5 |
| Fabric | Basis weight | g/m$^2$ | 52 | 52 | 52 | 52 | 52 | 52 | 52 | 52 | 52 | 52 | 52 | 52 |
| | Thickness | mm | 0.38 | 0.33 | 0.27 | 0.32 | 0.22 | 0.38 | 0.38 | 0.34 | 0.34 | 0.34 | 0.34 | 0.34 |
| | Bulk density | g/cm$^3$ | 0.139 | 0.158 | 0.193 | 0.163 | 0.236 | 0.139 | 0.137 | 0.156 | 0.156 | 0.156 | 0.156 | 0.156 |
| | MD direction flexural rigidity index | (gf·cm$^2$/cm)/(g/m$^2$)$^{2.5}$ | 15.6 | 25.6 | 29.7 | 19.0 | 37.4 | 15.6 | 15.8 | 11.0 | 10.0 | 9.0 | 12.0 | 12.0 |
| | CD direction flexural rigidity index | (gf·cm$^2$/cm)/(g/m$^2$)$^{2.5}$ | — | — | — | — | — | — | — | 8.02 | 8.53 | 9.03 | 7.52 | 8.02 |
| | Work of compression WC | gf·cm/cm$^2$ | 0.334 | 0.265 | 0.262 | 0.234 | 0.167 | 0.324 | 0.314 | 0.253 | 0.267 | 0.289 | 0.247 | 0.242 |
| | Recoverability of compression RC | % | 60 | 62 | 61 | 64 | 65 | 65 | 64 | 62 | 60 | 58 | 66 | 64 |
| | Water absorption parameter | — | 14.9 | 13.1 | 10.7 | 12.7 | 8.7 | 14.9 | 15.1 | 15.3 | 13.2 | 10.8 | 7.6 | 17.6 |

TABLE 3-continued

| | | Example | | | | | | | | | | | |
|---|---|---|---|---|---|---|---|---|---|---|---|---|
| Item | Unit | 25 | 26 | 27 | 28 | 29 | 30 | 31 | 32 | 33 | 34 | 35 | 36 |
| Handleability | — | 5 | 3 | 3 | 5 | 3 | 5 | 5 | 5 | 5 | 5 | 5 | 5 |
| Water absorption | times | 1.8 | 1.7 | 1.7 | 1.6 | 1.5 | 1.8 | 1.8 | 1.8 | 1.6 | 1.5 | 1.3 | 2.1 |
| Oil absorption | times | 6.1 | 5.6 | 5.6 | 5.5 | 4.9 | 6.2 | 6.2 | 6.0 | 5.6 | 5.3 | 5.0 | 6.3 |
| Ethanol liquid absorption | times | 5.0 | 4.6 | 4.6 | 4.5 | 4.0 | 5.1 | 5.1 | 4.9 | 4.6 | 4.3 | 4.1 | 5.2 |
| Cleaning ability sustainability | — | Good | Good | Good | Good | Good | Good | Good | Good | Good | Good | Good | Good |
| Industrial compostability | — | Good | Good | Good | Good | Good | Good | Good | Good | Good | Good | Good | Good |

TABLE 4

| | | | Example | | | | | | | | | |
|---|---|---|---|---|---|---|---|---|---|---|---|---|
| | Item | Unit | 37 | 38 | 39 | 40 | 41 | 42 | 43 | 44 | 45 | 46 |
| Structure/ Production Method | Single or two-component | — | Single component | Single component | Single component | Single component | Single component | Single component | Single component | Two component (blend) | Two component (blend) | Two component (blend) |
| | Fiber cross-section | — | V-shape | V-shape | V-shape | V-shape | V-shape | V-shape | V-shape | V-shape | V-shape | V-shape |
| | Resin | — | PLA | PLA | PLA | PHA | PBS | PGA | PA4 | PLA/PHA (PHA 10%) | PLA/PBS (PBS 10%) | PLA/Low melting point PLA (Low melting point PLA: 10%) |
| | Roller temperature | °C. | 100 | 100 | 100 | 90 | 80 | 180 | 220 | 135 | 135 | 135 |
| | Embossing linear pressure | N/mm | 20 | 20 | 20 | 20 | 20 | 20 | 20 | 20 | 20 | 20 |
| | Embossing temperature | m/min | 5 | 5 | 5 | 5 | 5 | 5 | 5 | 100 | 100 | 100 |
| | Embossing pattern | — | Pins | Pins | Pins | Pins | Pins | Pins | Pins | Pins | Pins | Pins |
| | Bonding area ratio | % | 8 | 8 | 8 | 8 | 8 | 8 | 8 | 8 | 8 | 8 |
| | Emboss depth | mm | 1.5 | 1.5 | 1.5 | 1.5 | 1.5 | 1.5 | 1.5 | 1.5 | 1.5 | 1.5 |
| | Embossing interval | mm | 4.43 | 4.43 | 4.43 | 4.43 | 4.43 | 4.43 | 4.43 | 4.43 | 4.43 | 4.43 |
| Fibers | Fineness | dtex | 2.3 | 2.3 | 2.3 | 2.3 | 2.3 | 2.3 | 2.3 | 2.3 | 2.3 | 2.3 |
| | Degree of irregularity | — | 1.6 | 1.6 | 1.6 | 1.6 | 1.6 | 1.6 | 1.6 | 1.6 | 1.6 | 1.6 |
| | Crimp number | crimps/inch | 20 | 22 | 24 | 18 | 18 | 18 | 18 | 18 | 18 | 18 |
| | Water absorption rate | wt % | 0.50 | 0.50 | 0.50 | 0.40 | 0.33 | 0.40 | 1.70 | 0.50 | 0.50 | 0.50 |
| | Angle formed | ° | 90 | 90 | 30 | 120 | 120 | 120 | 120 | 120 | 120 | 120 |

TABLE 4-continued

| | | | | | | | Example | | | | |
|---|---|---|---|---|---|---|---|---|---|---|---|
| Item | | Unit | 37 | 38 | 39 | 40 | 41 | 42 | 43 | 44 | 45 | 46 |
| | by V-shape Surface area of recessed part | $10^{-4}mm^2$ | 4.2 | 3.5 | 2.4 | 4.1 | 4.1 | 4.1 | 4.1 | 4.1 | 4.1 | 4.1 |
| Fabric | Basis weight | $g/m^2$ | 52 | 52 | 52 | 52 | 52 | 52 | 52 | 52 | 52 | 52 |
| | Thickness | mm | 0.34 | 0.34 | 0.21 | 0.30 | 0.34 | 0.30 | 0.31 | 0.27 | 0.29 | 0.27 |
| | Bulk density | $g/cm^3$ | 0.156 | 0.156 | 0.251 | 0.176 | 0.153 | 0.173 | 0.168 | 0.193 | 0.181 | 0.193 |
| | MD direction flexural rigidity index | $(gf \cdot cm^2/cm)/(g/m^2)^{2.5}$ | 11.0 | 10.0 | 14.4 | 12.6 | 12.3 | 12.8 | 13.3 | 15.9 | 15.6 | 15.2 |
| | CD direction flexural rigidity index | $(gf \cdot cm^2/cm)/(g/m^2)^{2.5}$ | 8.02 | 8.53 | 9.74 | 8.36 | 8.87 | 8.87 | 9.39 | 8.77 | 8.26 | 8.54 |
| | Work of compression WC | $gf \cdot cm/cm^2$ | 0.253 | 0.267 | 0.294 | 0.253 | 0.252 | 0.275 | 0.235 | 0.267 | 0.266 | 0.269 |
| | Recoverability of compression RC | % | 63 | 62 | 54 | 65 | 62 | 67 | 69 | 65 | 63 | 64 |
| | Water absorption parameter | — | 13.4 | 11.2 | 4.7 | 9.4 | 8.9 | 9.5 | 41.9 | 10.7 | 11.3 | 10.7 |
| | Handleability | — | 5 | 5 | 5 | 5 | 5 | 5 | 5 | 5 | 5 | 5 |
| | Water absorption | times | 1.8 | 1.6 | 1.3 | 1.6 | 1.7 | 1.6 | 1.4 | 1.6 | 1.6 | 1.7 |
| | Oil absorption | times | 5.9 | 5.5 | 4.4 | 5.2 | 5.9 | 5.2 | 4.9 | 5.2 | 5.6 | 5.7 |
| | Ethanol liquid absorption | times | 4.8 | 4.5 | 3.6 | 4.7 | 5.3 | 4.6 | 4.3 | 4.9 | 4.8 | 4.9 |
| | Cleaning ability sustainability | — | Good | Good | Good | Good | Good | Good | Good | Good | Good | Good |
| | Industrial compostability | — | Good | Good | Good | Good | Good | Good | Good | Excellent | Excellent | Excellent |

Comparative Examples 1 to 3

The filament non-woven fabrics of Comparative Examples 1 to 3 were obtained under the same production conditions as Example 39, except that polypropylene was used as the raw material and the basis weights were set to 35 to 77 g/m².

Comparative Examples 4 to 6

Polylactic acid was discharged from a spunbonding spinneret (round shape) at a spinning temperature of 220° C., and thermoplastic crimped fibers having an average fineness of 2.8 dtex were accumulated on a collection net. The transport speed was arbitrarily adjusted so that the total basis weight was 30 to 68 g/m², and thermocompression bonding was performed with an embossing roller of arbitrary embossing pattern, bonding area ratio, pitch, repeat, and depth at each basis weight at a constant temperature of 100° C./100° C. and a linear pressure of 20 N/mm to obtain the filament non-woven fabrics of Comparative Examples 4 to 6.

Comparative Example 7

The filament non-woven fabric of Comparative Example 7 was obtained using crimped fibers having an average fineness of 5.0 dtex using the production method of Example 6, except that the drawing force by the draw jet was further decreased.

Comparative Example 8

The filament non-woven fabric of Comparative Example 8 was obtained by changing the embossing pattern, bonding area ratio, pitch, repeat, and depth of the fiber structure of Example 6, and changing the transport speed so that the basis weight was 52 g/m².

Comparative Example 9

The filament non-woven fabric of Comparative Example 9 was obtained under the same production conditions as Example 7 except that the single-fiber cross-sectional shape (angle formed by V-shape) was changed.

As described above, the characteristics of the filament non-woven fabrics obtained in Comparative Examples 1 to 9 are shown in Table 5 below.

TABLE 5

| | Item | Unit | Comparative Example 1 | 2 | 3 | 4 | 5 | 6 | 7 | 8 | 9 |
|---|---|---|---|---|---|---|---|---|---|---|---|
| Structure/Production Method | Single or two-component | — | Single component | Single component | Single component | Single component | Single component | Single component | Single component | Single component | Single component |
| | Fiber cross-section | — | V-shape | V-shape | V-shape | Round | Round | Round | V-shape | V-shape | V-shape |
| | Resin | — | PP | PP | PP | PLA | PLA | PLA | PLA | PLA | PLA |
| | Roller temperature | °C. | 100 | 100 | 100 | 100 | 100 | 100 | 100 | 100 | 100 |
| | Embossing linear pressure | N/mm | 20 | 20 | 20 | 20 | 20 | 20 | 20 | 20 | 20 |
| | Embossing temperature | m/min | 5 | 5 | 5 | 5 | 5 | 5 | 5 | 5 | 5 |
| | Embossing pattern | — | Pins | Pins | Pins | Textured | Textured | Textured | Pins | Pins | Pins |
| | Bonding area ratio | % | 8 | 8 | 8 | 14.4 | 14.4 | 14.4 | 8 | 8 | 8 |
| | Emboss depth | mm | 1.5 | 1.5 | 1.5 | 0.33 | 0.33 | 0.33 | 1.5 | 0.33 | 1.5 |
| | Embossing interval | mm | 4.43 | 4.43 | 4.43 | 2 | 2 | 2 | 4.43 | 2 | 4.43 |
| Fibers | Fineness | dtex | 2.8 | 2.8 | 2.8 | 2.8 | 2.8 | 2.8 | 5.0 | 2.3 | 2.3 |
| | Degree of irregularity | — | 1.6 | 1.6 | 1.6 | 1 | 1 | 1 | 1.6 | 1.6 | 1.6 |
| | Crimp number | crimps/inch | 25 | 25 | 25 | 0 | 0 | 0 | 2 | 18 | 1 |
| | Water absorption rate | wt % | 0.02 | 0.02 | 0.02 | 0.50 | 0.50 | 0.50 | 0.50 | 0.50 | 0.50 |
| | Angle formed by V-shape | ° | 30 | 30 | 30 | — | — | — | 120 | 120 | 180 |
| | Surface area of recessed part | $10^{-4}$ mm² | 1.96 | 1.96 | 1.96 | — | — | — | 4.134 | 4.134 | — |
| Fabric | Basis weight | g/m² | 35 | 48 | 77 | 30 | 39 | 68 | 52 | 52 | 52 |
| | Thickness | mm | 0.36 | 0.43 | 0.66 | 0.15 | 0.18 | 0.24 | 0.22 | 0.21 | 0.20 |
| | Bulk density | g/cm³ | 0.097 | 0.113 | 0.116 | 0.197 | 0.219 | 0.281 | 0.239 | 0.251 | 0.260 |
| | MD direction flexural rigidity index | (gf·cm²/cm)/(g/m²)$^{2.5}$ | 6.7 | 7.6 | 6.4 | 39.9 | 46.4 | 42.6 | 39.0 | 41.0 | 13.3 |
| | CD direction flexural rigidity index | (gf·cm²/cm)/(g/m²)$^{2.5}$ | 2.1 | 2.9 | 5.0 | 15.3 | 18.4 | 20.4 | 22.1 | — | 8.2 |

TABLE 5-continued

| Item | Unit | Comparative Example | | | | | | | | |
|---|---|---|---|---|---|---|---|---|---|---|
| | | 1 | 2 | 3 | 4 | 5 | 6 | 7 | 8 | 9 |
| Work of compression WC | gf·cm/cm² | 0.934 | 0.703 | 0.616 | 0.079 | 0.082 | 0.080 | 0.093 | 0.100 | 0.069 |
| Recoverability of compression RC | % | 45 | 47 | 46 | 75 | 73 | 73 | 69 | 69 | 74 |
| Water absorption parameter | — | 0.40 | 0.35 | 0.34 | — | — | — | 8.67 | 8.23 | — |
| Handleability | — | 1 | 2 | 1 | 2 | 1 | 1 | 2 | 1 | 1 |
| Water absorption | times | 0.1 | 0.2 | 0.2 | 1.3 | 0.8 | 0.7 | 1.36 | 1.34 | 0.71 |
| Oil absorption | times | 17.8 | 14.0 | 9.0 | 3.3 | 3.5 | 2.2 | 4.62 | 4.52 | 3.20 |
| Ethanol liquid absorption | times | 18.9 | 13.2 | 8.1 | 3.1 | 2.1 | 1.8 | 3.8 | 3.70 | 2.90 |
| Cleaning ability sustainability | — | OK | OK | OK | Good | Good | Good | Good | Good | Good |
| Industrial compostability | — | Poor | Poor | Poor | Good | Good | Good | Good | Good | Good |

INDUSTRIAL APPLICABILITY

Since the non-woven fabric of the present invention has both good handleability and high water absorption, it can suitably be used as a cleaning wipe, a diaper top sheet or back sheet, or a packaging material (in particular, a food packaging material for microwave ovens, which generate moisture).

The invention claimed is:

1. A non-woven fabric comprising a thermoplastic biodegradable resin, wherein fibers constituting the non-woven fabric have crimps, a machine direction (MD) flexural rigidity index of the non-woven fabric as defined by the following formula is 7.77 to 37.4:

machine direction (MD) flexural rigidity index=machine direction (MD) flexural rigidity (gf·cm)/{basis weight (g/m²)}$^{2.5}$×10$^6$, and a bulk density of the non-woven fabric is 0.098 g/cm³ to 0.251 g/cm³, and
wherein the fibers have a degree of deformation of 1.2 to 2.2, and
the fibers constituting the non-woven fabric each have at least one recessed part inside a crimp in a single-fiber cross section, and a water absorption parameter as defined by the following formula is 4.7 or more:
water absorption parameter=W×S/B where W (wt %) is a water absorption rate of the fibers, B (g/cm³) is a bulk density of the non-woven fabric, and S (10$^{-4}$ mm²) is a cross-sectional area of the recessed part.

2. The non-woven fabric according to claim 1, wherein the non-woven fabric has partially-bonded embossed parts, an interval of the embossed parts is 2.0 mm or more, and a bonding area ratio is 3% to 40%.

3. The non-woven fabric according to claim 1, wherein a work of compression WC of the non-woven fabric is 0.1 gf·cm/cm² or more.

4. The non-woven fabric according to claim 1, wherein a recoverability of compression RC of the non-woven fabric is 48% or more.

5. The non-woven fabric according to claim 1, wherein a basis weight of the non-woven fabric is 10 g/m² to 100 g/m².

6. The non-woven fabric according to claim 1, wherein the thermoplastic biodegradable resin is one selected from the group consisting of polylactic acid, polyhydroxyalkanoic acid, polyhydroxybutyrate variate, polyhydroxybutyrate hexanoate, nylon 4, polycaprolactone, polybutylene succinate, polybutylene succinate adipate, polybutylene terephthalate succinate, polybutylene succinate carbonate, polybutylene adipate terephthalate, polyethylene succinate, polyethylene terephthalate succinate, polyglycolic acid, and polyvinyl alcohol.

7. The non-woven fabric according to claim 1, wherein the thermoplastic biodegradable resin is two or more selected from the group consisting of polylactic acid, polyhydroxyalkanoic acid, polyhydroxybutyrate variate, polyhydroxybutyrate hexanoate, nylon 4, polycaprolactone, polybutylene succinate, polybutylene succinate adipate, polybutylene terephthalate succinate, polybutylene succinate carbonate, polybutylene adipate terephthalate, polyethylene succinate, polyethylene terephthalate succinate, polyglycolic acid, and polyvinyl alcohol.

8. The non-woven fabric according to claim 1, wherein the non-woven fabric is a filament non-woven fabric.

9. A cleaning wipe comprising the non-woven fabric according to claim 1.

* * * * *